United States Patent [19]

Connor et al.

[11] B 4,001,398

[45] Jan. 4, 1977

[54] **OCTAHYDRO AND DECAHYDRO DERIVATIVES OF ACID S, AN ANTIBIOTIC PRODUCED BY *POLYANGIUM CELLULOSUM* VAR. FULVUM**

[75] Inventors: David T. Connor, Parsippany; Samuel M. Ringel, Rockaway; Sidney Roemer, Flanders; Maximilian von Strandtmann, Rockaway Township, all of N.J.

[73] Assignee: Warner-Lambert Company, Morris Plains, N.J.

[22] Filed: June 24, 1974

[21] Appl. No.: 482,058

[44] Published under the second Trial Voluntary Protest Program on March 2, 1976 as document No. B 482,058.

[52] U.S. Cl. ............................................. 424/122
[51] Int. Cl.$^2$ ...................................... A61K 35/00
[58] Field of Search .................................. 424/122

[56] References Cited

UNITED STATES PATENTS

| 3,651,216 | 3/1972 | Ringel et al. | 424/115 |
| 3,804,948 | 4/1974 | Strandtmann et al. | 424/122 |

*Primary Examiner*—Jerome D. Goldberg
*Attorney, Agent, or Firm*—Albert H. Graddis; Frank S. Chow

[57] ABSTRACT

The present invention describes octahydro and decahydro derivatives of the novel antibiotic substance, acid S, produced by the organism *Polyangium cellulosum* var. fulvum (ATCC No. 25532) and to processes for their preparation. The octahydro and dechydro derivatives of acid S of this invention are useful as antifungal and antibacterial agents.

14 Claims, 5 Drawing Figures

Fig. 1.
Octahydrotrial S

Fig. 3. Decahydroacid S

OCTAHYDRO AND DECAHYDRO DERIVATIVES OF ACID S, AN ANTIBIOTIC PRODUCED BY POLYANGIUM CELLULOSUM VAR. FULVUM

The present invention relates to novel octahydro and decahydro derivatives of acid S, a potent antibiotic produced by fermentation of the microorganism *Polyangium cellulosum* var. fulvum (ATCC No. 25532) in an appropriate culture medium. Specifically, the present invention relates to octahydroacid S, octahydroacid S methyl ester and octahydrotriol S, having molecular formulas, $C_{27}H_{47}O_2(OH)_2CO_2H$, $C_{27}H_{47}O_2(OH)_2CO_2CH_3$ and $C_{27}H_{47}O_2(OH)_2CH_2OH$, respectively, and to the corresponding acetates, octahydroacid S diacetate, octahydroacid S methyl ester diacetate and octahydrotriol S triacetate, having molecular formulas, $C_{27}H_{47}O_2(OCOCH_3)_2CO_2H$, $C_{27}H_{47}O_2(OCOCH_3)_2CO_2CH_3$ and $C_{27}H_{47}O_2(OCOCH_3)_2CH_2OCOCH_3$, respectively. The present invention also specifically relates to decahydroacid S, decahydroacid S methyl ester and decahydrotriol S, having molecular formulas, $C_{27}H_{49}O_2(OH)_2CO_2H$, $C_{27}H_{49}O_2(OH)_2CO_2CH_3$ and $C_{27}H_{49}O_2(OH)_2CH_2OH$, respectively, to the corresponding acetates, decahydroacid S diacetate, decahydroacid S methyl ester diacetate and decahydrotriol S triacetate, having molecular formulas, $C_{27}H_{49}O_2(OCOCH_3)_2CO_2H$, $C_{27}H_{49}O_2(OCOCH_3)_2CO_2CH_3$ and $C_{27}H_{49}O_2(OCOCH_3)_2CH_2OCOCH_3$, respectively. Acid S diacetate, having molecular formula $C_{27}H_{39}O_2(OCOCH_3)_2CO_2H$, and acid S methyl ester diacetate, having molecular formula $C_{27}H_{39}O_2(OCOCH_3)_2CO_2CH_3$, are also included within the scope of the present invention.

The present invention also relates to processes for the preparation of the aforementioned octahydro and decahydro derivatives of acid S and to pharmaceutical compositions exhibiting antifungal and antibacterial activity.

Antibiotics designated A, B and C and antibiotic substances designated acids F and S and components B and C, produced when the microorganism *Polyangium cellulosum* var. fulvum (ATCC No. 25532) is fermented in a suitable culture medium, are disclosed in U.S. Pat. No. 3,651,216, issued Mar. 21, 1972 and U.S. Pat. No. 3,804,948, issued Apr. 16, 1974. Antibiotics B and C and acids F and S are effective against a variety of fungi, such as the yeast phase of *Histoplasma capsulatum*, *Microsporum fulvum* and *Trichophyton mentagrophytes*, ineffective against a panel of gram negative and gram positive bacteria, such as *Enterobacter aerogenes*, *Mycobacterium phlei*, *Proteus mirabilis*, *Proteus vulgaris*, *Psuedomonas aeruginosa*, *Staphylococcus aureus*, *Streptococcus faecalis* and *Escherichia coli*, and are effective against *Diplococcus pneumoniae* and *Streptococcus pyogenes*, gram positive bacteria.

We have found that hydrogenation of acid S gives a series of octahydro and decahydro derivatives of acid S, the compounds of this invention, which like the aforementioned antibiotics show both antifungal and selective antibacterial activity. The compounds of this invention, are more active antibacterial agents than acids F and S and are thus indicated for the treatment of both susceptible antibacterial and antifungal infections.

The octahydro derivatives of acid S of the present invention are prepared by the processes shown below:

The production of acid S by fermentation of *Polyangium cellulosum* var. fulvum in a suitable culture medium and its conversion to the corresponding methyl ester are described in U.S. Pat. Nos. 3,651,216 and 3,804,948.

Octahydroacid S methyl ester is obtained when acid S methyl ester is hydrogenated in a suitable solvent in the presence of a noble metal catalyst at about room temperature and at about atmospheric pressure. Typically, acid S methyl ester is treated with hydrogen in an alcoholic solvent, such as absolute ethanol, in the presence of 10 percent palladium-on-carbon at room temperature and atmospheric pressure until the absorption of hydrogen ceases to give octahydroacid S methyl ester. To produce octahydrotriol S, octahydroacid S methyl ester is reduced with a complex metal hydride in an ethereal solvent. Generally, octahydroacid S methyl ester is treated with lithium aluminum hydride in boiling tetrahydrofuran under a blanket of nitrogen to afford octahydrotriol S. To secure octahydroacid S, octahydroacid S methyl ester is hydrolyzed with an alkali metal hydroxide in a suitable solvent. Typically, octahydroacid S methyl ester is treated with a boiling dilute aqueous solution of sodium hydroxide, preferably 5 percent aqueous sodium hydroxide, under an atmosphere of nitrogen to yield octahydroacid S.

Octahydroacid S diacetate, octahydroacid S methyl ester diacetate and octahydrotriol S triacetate are prepared by treatment of octahydroacid S, octahydroacid S methyl ester and octahydrotriol S, respectively, with acetic anhydride and a tertiary amine, such as pyridine, as the acid-acceptor.

The aforementioned octahydro derivatives of acid S were recovered from the respective reaction mixtures by methods wellknown to those skilled in the art of organic chemistry.

The decahydro derivatives of acid S of the present invention are produced by the processes shown below:

$$\text{Acid S} \xrightarrow[\text{Pd-C}]{H_2} \text{Decahydroacid S} \xrightarrow[\text{pyridine}]{(CH_3CO)_2O} \text{Decahydroacid S Diacetate}$$
$$C_{27}H_{39}O_2(OH)_2CO_2H \quad\quad C_{27}H_{49}O_2(OH)_2CO_2H \quad\quad C_{27}H_{49}O_2OCOCH_3)_2CO_2H$$

$$\downarrow CH_2N_2$$

$$\text{Decahydroacid S Methyl Ester} \xrightarrow[\text{pyridine}]{(CH_3CO)_2O} \text{Decahydroacid S Methyl Ester Diacetate}$$
$$C_{27}H_{49}O_2(OH)_2CO_2CH_3 \quad\quad\quad C_{27}H_{49}O_2(OCOCH_3)_2CO_2CH_3$$

$$\text{Triol S} \xrightarrow[\text{Pd-C}]{H_2} \text{Decahydrotriol S} \xrightarrow[\text{pyridine}]{(CH_3CO)_2O} \text{Decahydrotriol S Triacetate}$$
$$C_{27}H_{39}O_2(OH)_2CH_2OH \quad C_{27}H_{49}O_2(OH)_2CH_2OH \quad C_{27}H_{49}O_2(OCOCH_3)_2CH_2OCOCH_3$$

To obtain the decahydro derivatives of acid S, acid S is treated with hydrogen in a suitable solvent at about room temperature and atmospheric pressure in the presence of a noble metal hydrogenation catalyst. Typically, a solution of acid S and an alcoholic solvent, such as ethanol, is hydrogenated at room temperature and atmospheric pressure in the presence of 10 percent palladium-on-carbon. The hydrogenation is allowed to proceed until there is no further uptake of hydrogen. Decahydroacid S methyl ester is prepared by esterification of acid S with ethereal diazomethane in a suitable alcoholic solvent, such as absolute ethanol. The diacetates of decahydroacid S and decahydroacid S methyl ester are prepared by acetylation with acetic anhydride in the presence of a tertiary amine, such as pyridine, as the acid-acceptor.

Triol S and the process for its production are described in our copending patent application No. Decahydrotriol S is obtained when triol S is hydrogenated in a suitable solvent at about atmospheric pressure and room temperature in the presence of a noble metal catalyst. Generally, a solution of triol S and an alcoholic solvent, such as absolute ethanol, is treated with hydrogen at atmospheric pressure and room temperature in the presence of 10 percent palladium-on-carbon until there is no additional uptake of hydrogen to yield decahydrotriol S. Decahydrotriol S is converted into decahydrotriol S triacetate when the aforementioned triol is treated with acetic anhydride in the presence of a tertiary amine acid-acceptor. Pyridine is generally employed as the acid-acceptor.

The decahydro derivatives of acid S of this invention are conveniently recovered from the respective reaction mixtures by techniques well-known to those skilled in the art of synthetic organic chemistry.

The compounds of the present invention are characterized by infrared spectroscopy, mass spectrometry and diagnostic thin-layer chromatography.

The infrared spectra of the octahydro and decahydro derivatives of acid S of this invention are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

The infrared spectra of representative octahydro and decahydro derivatives of acid S are illustrated in FIGS. 1, 2, 3, and 4. The infrared spectra of acid S diacetate is illustrated in FIG. 5.

Figure 1:
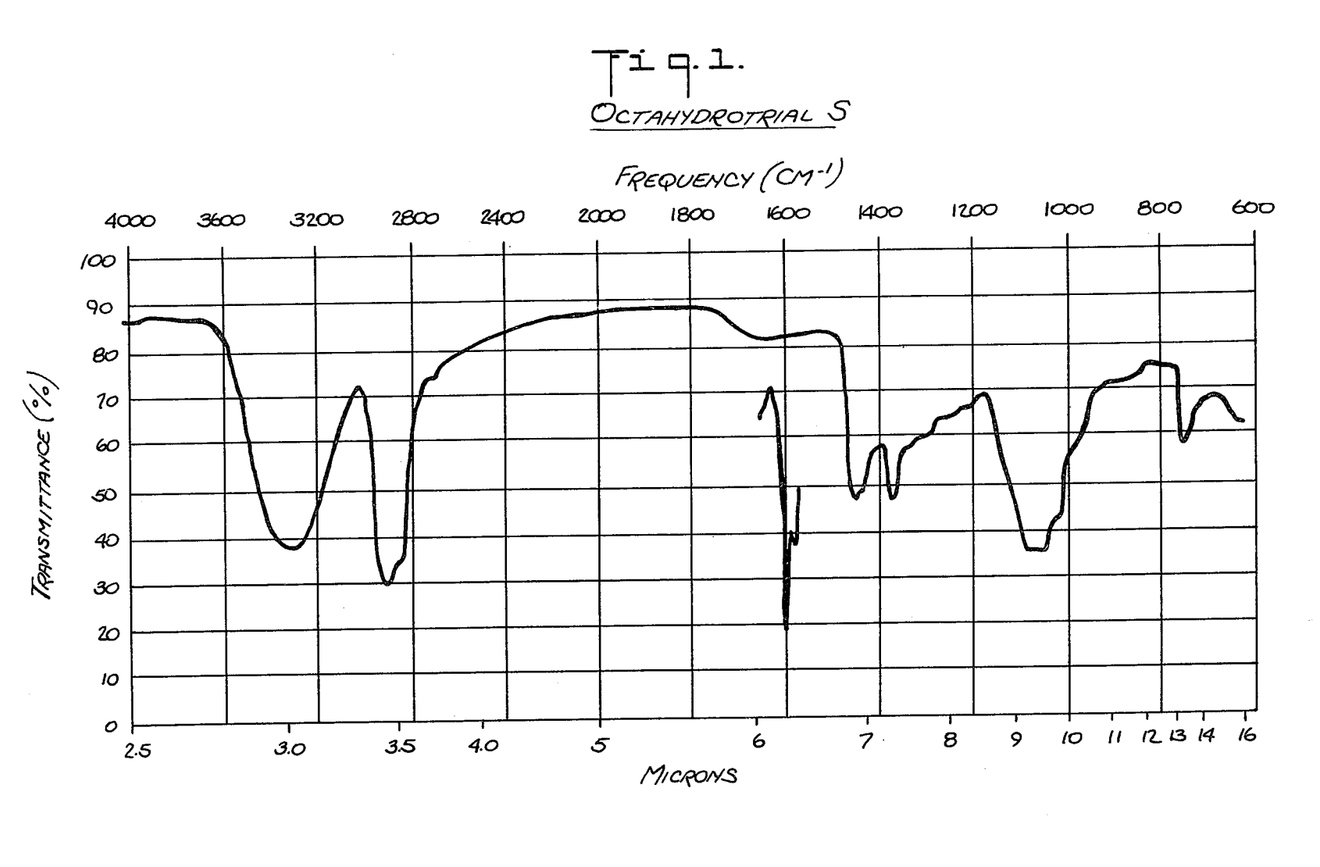
Figure 2:
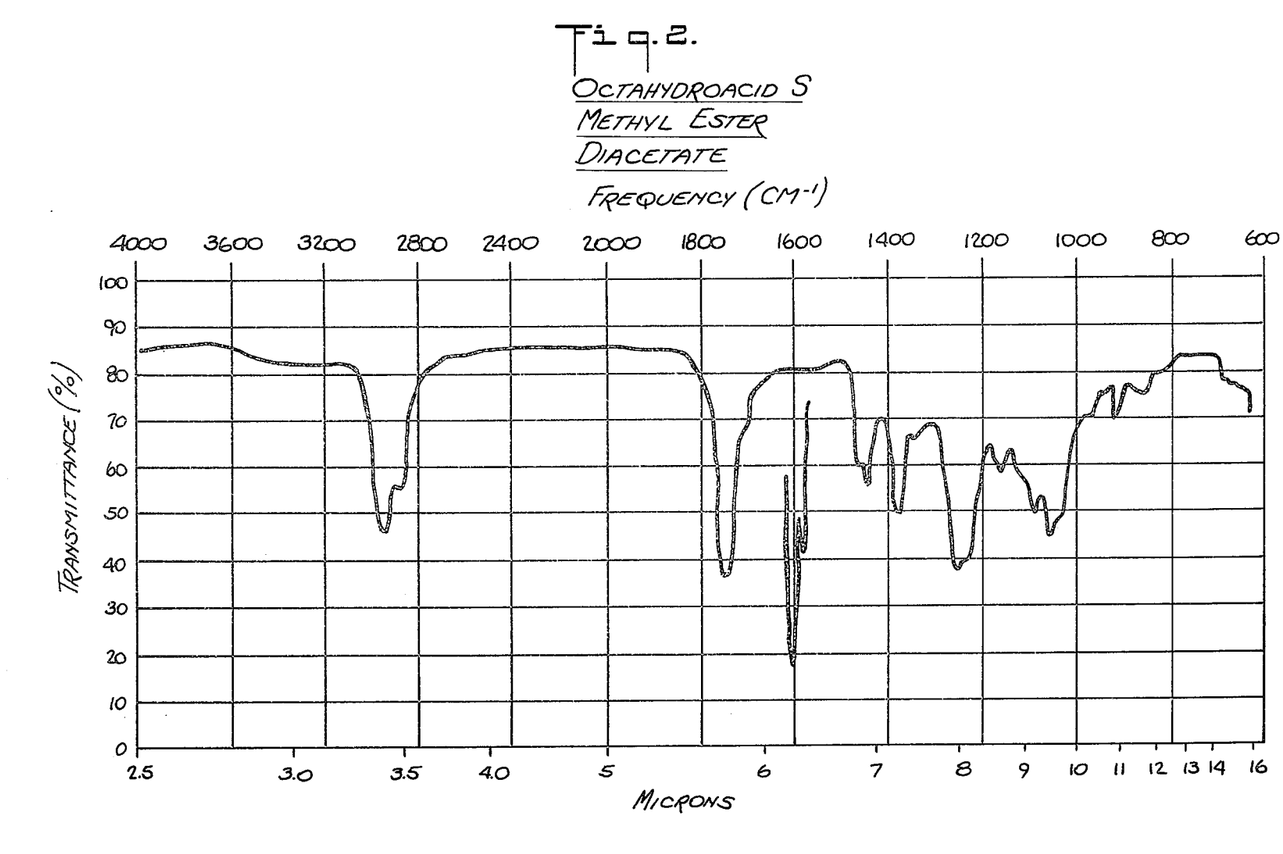
Figure 3:
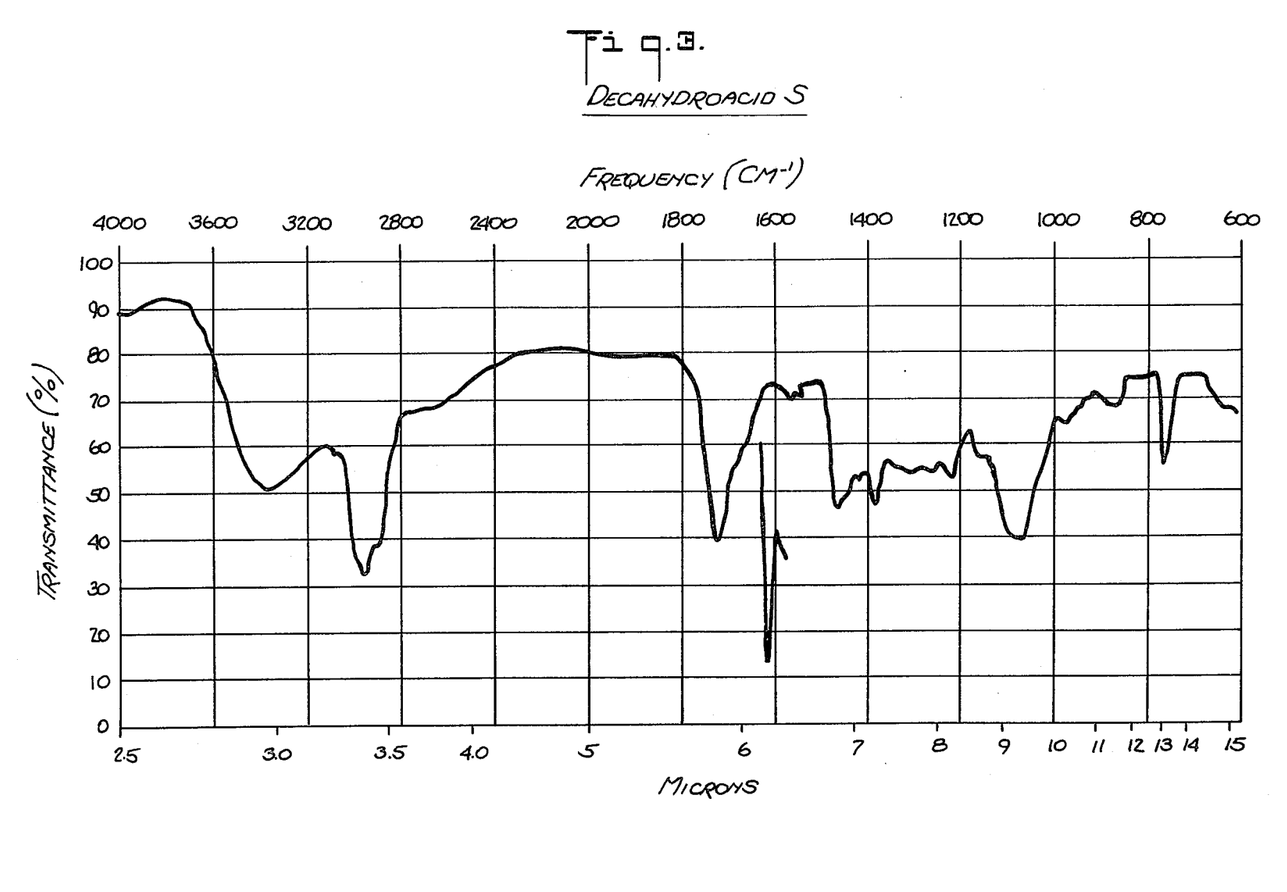
Figure 4:
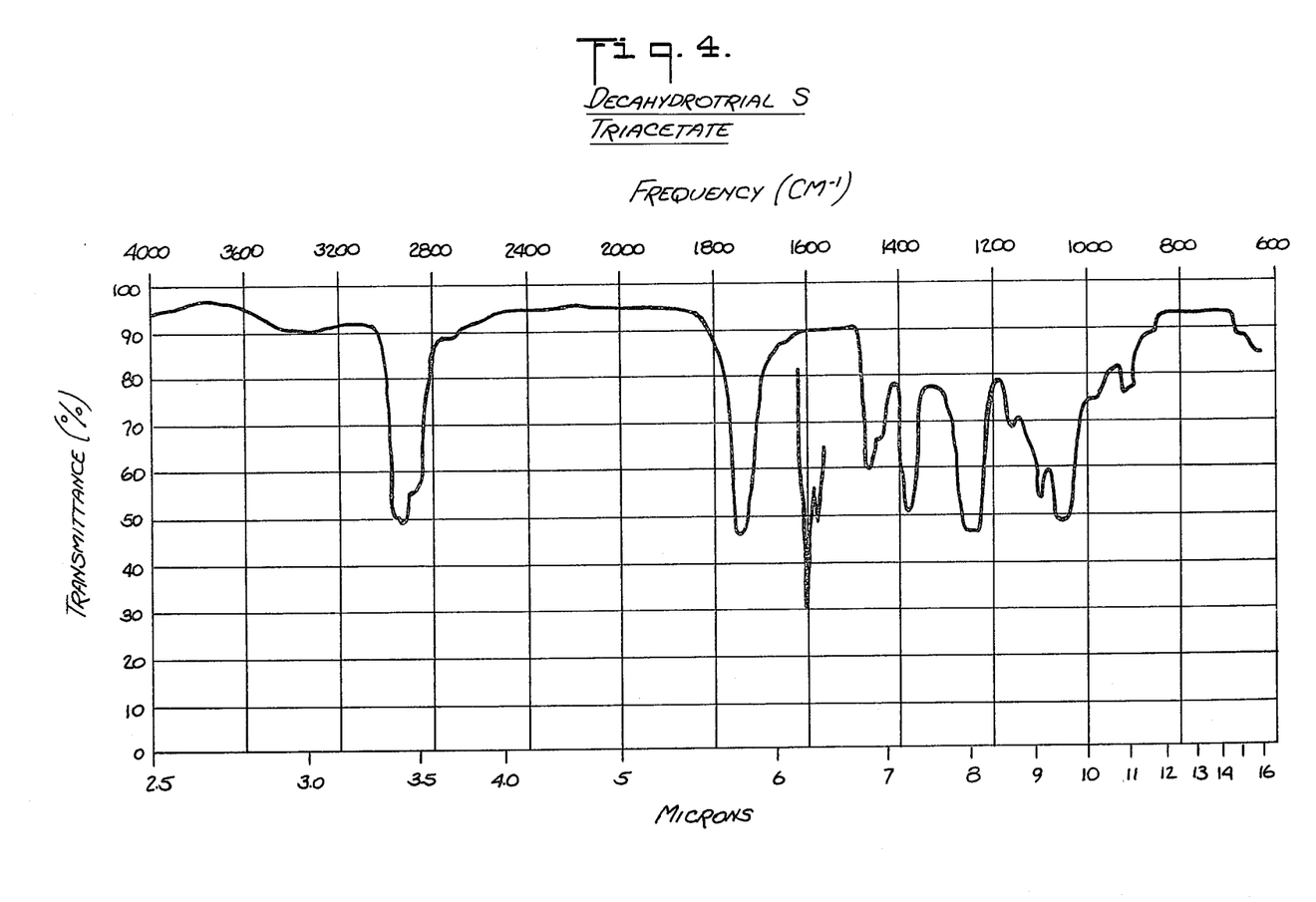
Figure 5:
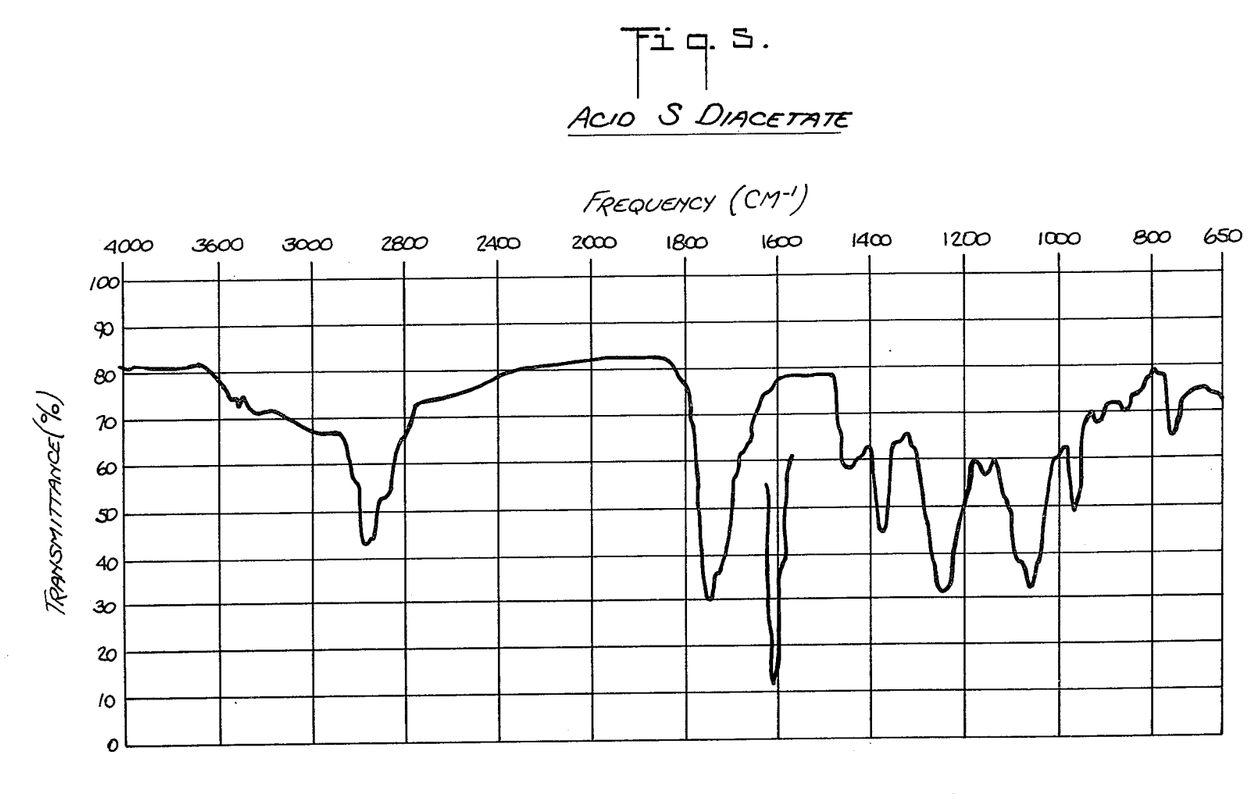

The mass spectra of the octahydro and decahydro derivatives of acid S of this invention are measured on a double-focusing high resolution mass spectrometer utilizing a heated direct insertion probe. The molecular composition of the parent peaks are determined by employing perfluorotributylamine (mass spectral grade, available from PCR, Inc., Gainsville, Florida) as the internal standard and peak matching techniques well-known to those skilled in the art. The application of these mass spectral techniques permits not only the determination of the molecular composition of the parent ion and confirmation of the postulated transformations, but, like the aforementioned infrared measurements, provides a definitive physical property useful for identification purposes.

The octahydro and decahydro derivatives of acid S of this invention are examined on thin-layers of silica gel using 85:10:5 ethyl acetate: 2-propanol: water as the solvent system and iodine as the visualization agent. The aforementioned derivatives of acid S appear as one well-defined spot.

The diacetates of acid S and acid S methyl ester are obtained when acid S and acid S methyl ester are acetylated with acetic anhydride in the presence of a tertiary amine acid-acceptor such as pyridine. Like the octahydro and decahydro derivatives of acid S of this invention, the aforementioned diacetates are identified by characteristic infrared absorption bands and mass spectral mass-to-charge values, and showed one well-defined spot on thin-layers of silica gel when examined using the hereinbefore mentioned solvent system and visualization agent.

The molecular formulas of octahydroacid S and decahydroacid S are calculable from the molecular ions of the corresponding diacetates.

The octa- and decahydro derivatives of acid S the acetates thereof, and acid S diacetate and acid S methyl ester diacetate, the compounds of this invention, inhibit the growth of fungi, such as of yeast phase of *Histoplasma capsulatum*, at minimum inhibitory concentrations falling within the range of 6.25 to 50 micrograms/milliliter, when evaluated by the in vitro tube dilution technique described in U.S. Pat. No. 3,651,216. Thus the compounds of the present invention are useful for the treatment of dermatophytic and systemic fungal disease.

The compounds of this invention exhibit selective antibacterial activity. When evaluated by the antibacterial tube dilution technique described in Example 15, the aforementioned compounds inhibit the growth of *Diplococcus pneumoniae* and *Streptococcus pyogenes* at minimum inhibitory concentrations in the range of 3.12 to 6.25 micrograms/milliliter, and are virtually inactive against a panel of bacteria, including *Proteus vulgaris*,

*Escherichia coli* and *Staphylococcus aureus*. Thus the compounds of this invention are useful selective antibacterial agents.

The antimicrobial compounds of this invention can be formulated with inert excipients into various dosage forms for oral, parenteral and topical administration by methods well-known to those skilled in the pharmacist's art. Tablets, capsules, powders, solutions, suspensions, ointments, gels and creams are included among these dosage forms. For topical administration, the instant compounds may be blended with a vehicle such as white petroleum, the weight of the active ingredients being from about 0.1 to 50 percent of the total weight.

The antimicrobial octahydro and decahydro derivatives of acid S, acid S diacetate and acid S methyl ester diacetate of this invention can be administered orally, parenterally or topically to various mammals, such as dogs, cats and guinea pigs, afflicted with fungal and/or bacterial disease. The typical dose is about 0.01 to 100 mg/kg of body weight of the animal.

The following examples are included to further illustrate the invention and are not to be construed as limiting the scope of the invention:

EXAMPLE 1

Octahydroacid S

A solution of octahydroacid S methyl ester (50 mg) in 5 percent aqueous sodium hydroxide (2 ml) was refluxed under nitrogen for 30 minutes. The reaction mixture was cooled, acidified with dilute hydrochloric acid and extracted with chloroform. The extracts were dried over $MgSO_4$ and evaporated to give a colorless oil (31 mg).

Infrared Spectrum: $\nu_{max}$ 3350, 1720, 1460, 1380, 1080 and 770 $cm^{-1}$.

Mass Spectrum: The diacetate of octahydroacid S gave the correct molecular ion.

EXAMPLE 2

Octahydroacid S Methyl Ester

A solution of acid S methyl ester (150 mg) in absolute ethanol (20 ml) was hydrogenated over 10 percent palladium-on-carbon for 3 hours. The catalyst was filtered off and the filtrate was evaporated to give a colorless oil. Purification by preparative t.l.c. gave the product as a colorless oil (72 mg).

Infrared Spectrum: $\nu_{max}$ 3350, 1740, 1440, 1380, 1210 and 1080 $cm^{-1}$.

Mass Spectrum: observed molecular ion, 496.3792; calculated for $C_{29}H_{52}O_6$, 496.3764 m/e (relative intensity) 498 (0.5), 496 (4.5), 494 (1.8), 167 (37), 154 (100), 127 (14) and 109 (11).

EXAMPLE 3

Octahydrotriol S

Excess lithium aluminum hydride was added to a solution of octahydroacid S methyl ester (50 mg) in tetrahydrofuran (20 ml). The reaction mixture was refluxed with stirring under nitrogen for 3 hours. The reaction mixture was cooled, a few drops of water were added to decompose the excess lithium aluminum hydride followed by 50 mg of magnesium sulfate. The inorganic solids were filtered off and washed thoroughly with $CHCl_3$. The filtrate and washings were evaporated to give a colorless oil. Purification by preparative t.l.c. gave a pure homogeneous product as a colorless oil.

Infrared Spectrum: $\nu_{max}$ 3300, 1450, 1370, 1060 and 750 $cm^{-1}$.

Mass Spectrum: m/e (relative intensity) 470 (11), 468 (44), 466 (33), 167 (62), 154 (100), 127 (20) and 109 (20).

EXAMPLE 4

Octahydroacid S Diacetate

Octahydroacid S was acetylated with acetic anhydride in pyridine at room temperature overnight. The solvents were removed under reduced pressure to give a yellow oil. Diagnostic t.l.c. indicated a pure homogeneous product.

Infrared Spectrum: $\nu_{max}$ 1740, 1450, 1370, 1240, 1050, 760 and 710 $cm^{-1}$.

Mass Spectrum: observed molecular ion, 566.3847; calculated for $C_{32}H_{54}O_8$, 566.3820 m/e (relative intensity) 568 (1), 566 (8), 564 (7), 469 (3), 409 (1), 349 (1), 167 (100), 154 (42), 127 (19) and 109 (19).

EXAMPLE 5

Octahydroacid S Methyl Ester Diacetate

Octahydroacid S methyl ester was acetylated with acetic anhydride in pyridine at room temperature overnight. The reaction was worked up in the usual way to give a colorless oil. Diagnostic t.l.c. indicated a pure homogeneous product.

Infrared Spectrum: $\nu_{max}$ 1740, 1440, 1370, 1250, 1230, 1050 and 920 $cm^{-1}$.

Mass Spectrum m/e (relative intensity) 582 (5), 580 (20), 578 (7), 520 (15), 460 (15), 367 (12), 337 (17), 214 (45), 197 (35), 167 (100), 154 (100) 143 (50), 127 (50) and 109 (45).

EXAMPLE 6

Octahydrotriol S Triacetate

Octahydrotriol S was acetylated with acetic anhydride in pyridine at room temperature overnight. The reaction mixture was cooled and methanol was added to decompose the excess acetic anhydride. The solvents were removed under reduced pressure to give a colorless oil. Diagnostic t.l.c. indicated a pure homogeneous product.

Infrared Spectrum: $\nu_{max}$ 1740, 1450, 1370, 1240, 1300 and 1240 $cm^{-1}$.

Mass Spectrum: m/e (relative intensity) 596 (1), 594 (4), 592 (2), 167 (83), 154 (100), 127 (22) and 109 (16).

EXAMPLE 7

Decahydroacid S

A solution of acid S (50 mg) in absolute ethanol (20 ml) was hydrogenated over 10 percent palladium-on-carbon for 4 hours. The catalyst was filtered off and the filtrate evaporated to give a colorless oil. Purification by preparative t.l.c. gave the product as a colorless oil (20 mg).

Infrared Spectrum: $\nu_{max}$ 3350, 1720, 1470, 1380, 1080 and 960 $cm^{-1}$.

Mass Spectrum:

The mass spectrum of the diacetate prepared for this acid gives the correct molecular ion.

EXAMPLE 8

Decahydroacid S Methyl Ester

Decahydroacid S was dissolved in absolute ethanol and methylated with ethereal diazomethane. Purification by preparative t.l.c. gave a pure homogeneous product was a colorless oil.

Infrared Spectrum: $\nu_{max}$ 3350, 1740, 1470, 1450, 1380, 1210 and 1080 cm$^{-1}$.

Mass Spectrum: m/e (relative intensity) 498 (4), 373 (2), 339 (7), 167 (9), 154 (63), 142 (14), 127 (100) and 109 (34).

EXAMPLE 9

Decahydrotriol S

Triol S (47 mg) in absolute ethanol (20 ml) was hydrogenated over 10 percent palladium-on-carbon for 3 hours. The catalyst was filtered off and the solvent evaporated under reduced pressure to give a colorless oil. Purification by preparative t.l.c. gave a pure homogeneous product as a colorless oil (16 mg).

Infrared Spectrum: $\nu_{max}$ 3350, 1470, 1390 and 1080 cm$^{-1}$.

Mass Spectrum: m/e (relative intensity) 470 (4), 339 (7), 315 (4), 297 (6), 154 (15), 127 (100) and 109 (60).

EXAMPLE 10

Decahydroacid S Diacetate

Decahydroacid S was acetylated with acetic anhydride and pyridine at room temperature overnight. The reaction mixture was poured onto ice-water. The resulting solution was extracted with CHCl$_3$. The CHCl$_3$ extracts were dried over MgSO$_4$ and evaporated to give a colorless oil. Diagnostic t.l.c. indicated a pure product.

Infrared Spectrum: $\nu_{max}$ 1740, 1470, 1380, 1250 and 1060 cm$^{-1}$.

Mass Spectrum: m/e (relative intensity) 568 (12.5), 167 (20), 154 (70 ), 127 (100 ) and 109 (60).

EXAMPLE 11

Decahydroacid S Methyl Ester Diacetate

Decahydroacid S methyl ester was acetylated by the method described for the preparation of octahydroacid S diacetate. The product was obtained as a colorless oil.

Infrared Spectrum: $\nu_{max}$ 1740, 1470, 1440, 1380, 1240, 1090, 1050 and 920 cm$^{-1}$.

Mass Spectrum: observed molecular ion; 582.4130, calculated for C$_{33}$H$_{58}$O$_8$, 582.4131 m/e (relative intensity) 582 (8), 522 (4), 506 (1), 367 (5), 223 (5), 201 (4), 167 (8), 154 (36), 127 (100) and 109 (36).

EXAMPLE 12

Decahydrotriol S Triacetate

Decahydrotriol S was acetylated by the method described for the preparation of octahydroacid S diacetate. The product was obtained as a colorless oil. Diagnostic t.l.c. indicated a pure homogeneous product.

Infrared Spectrum: $\nu_{max}$ 1740, 1460, 1380, 1240, 1090, 1040 and 910 cm$^{-1}$.

Mass Spectrum: observed molecular ion, 596.4355; calculated for C$_{34}$H$_{60}$O$_8$, 596.4288 m/e (relative intensity) 596 (6), 536 (5), 520 (2), 476 (3), 462 (4), 441 (4), 381 (3.5), 237 (4), 215 (4), 199 (18), 167 (7), 154 (25), 127 (100) and 109 (42).

EXAMPLE 13

Acid S Diacetate

Acid S was acetylated with acetic anhydride in pyridine at room temperature overnight. The solvents were removed under reduced pressure to give the crude product. Preparative thinlayer chromatography gave the product as a colorless oil.

Infrared Spectrum: 1745 cm$^{-1}$ (C=O of acetates) 1720 (C=O of acid).

Mass Spectrum: m/e (relative intensity) 558 (10), 529 (32), 463 (14), 345 (7), 245 (32), 193 (100) and 165 (57).

EXAMPLE 14

Acid S Methyl Ester Diacetate

Acid S methyl ester was acetylated by the method described for acid S. The product was a colorless oil shown to be homogeneous by diagnostic thin-layer chromatography.

Infrared Spectrum: $\nu_{max}$ 1760, 1440, 1370, 1240, 1050 and 960 cm$^{-1}$.

Mass Spectrum: m/e (relative intensity), 572 (23), 543 (53), 477 (29), 259 (35) and 193 (100).

EXAMPLE 15

Quantitative in vitro Antibacterial Procedure

One ml volumes of brain heart infusion broth, usually starting with 50 $\mu$g/ml compound were diluted through nine tubes and each tube inoculated with 0.1 ml of an overnight broth culture standardized to 90 percent light transmittancy at 650 nm. After 48 hours incubation at 37°C, the lowest concentration of compound showing no visible growth was recorded as the minimal inhibitory concentration.

We claim:

1. An antimicrobial substance, octahydroacid S, prepared by treating octahydroacid S methyl ester (1 equivalent) with 5 percent aqueous sodium hydroxide solution (50 equivalents) for 30 minutes at 100° and having the following characteristics:
   a. Molecular Formula C$_{28}$H$_{50}$O$_6$; molecular weight 482.
   b. Infrared Spectrum $\nu_{max}$ 3350, 1720, 1460, 1380, 1080 and 720 cm$^{-1}$.

2. An antimicrobial substance, octahydroacid S methyl ester, prepared by stirring a 1 percent ethanolic solution of acid S methyl ester with hydrogen in the presence of 10% palladium-on-carbon for 3 hours and having the following characteristics:
   a. Infrared Spectrum $\nu_{max}$ 3350, 1740, 1440, 1380, 1210 and 1080 cm$^{-1}$.
   b. Mass Spectrum m/e (relative intensity) 498 (0.5), 496 (4.5), 494 (1.8), 167 (37), 154 (100), 127 (14) and 109 (11). molecular observed ion: 496.3792; calculated for C$_{29}$H$_{52}$O$_6$ : 496.3764.

3. An antimicrobial substance, octahydrotriol S, prepared by treating octahydroacid S methyl ester (1 equivalent) with lithium aluminum hydride (10 equivalents) in the presence of boiling tetrahydrofuran (400 equivalents) for 3 hours and having the following characteristics:
   a. Infrared Spectrum $\nu_{max}$ 3300, 1450, 1320, 1060 and 750 cm$^{-1}$.

b. Mass Spectrum m/e (relative intensity) 470 (11), 468 (44), 466 (33), 167 (62), 154 (100), 127 (20) and 109 (20).

c. Molecular Formula $C_{28}H_{52}O_5$; molecular weight 468.

4. An antimicrobial substance, octahydroacid S diacetate, prepared by treating octahydroacid S (1 equivalent) with acetic anhydride (100 equivalents) and pyridine (200 equivalents) at room temperature for 16 hours, and having the following characteristics:
   a. Infrared Spectrum $\nu_{max}$ 1740, 1450, 1370, 1240, 1050, 760 and 710 cm$^{-1}$.
   b. Mass Spectrum m/e (relative intensity) 568 (1), 566 (8), 564 (7), 469 (3), 409 (1), 349 (1), 167 (100), 154 (42), 127 (19) and 109 (19); molecular ion observed: 566.3847; calculated for $C_{32}H_{54}O_8$: 566.3820.

5. An antimicrobial substance, octahydroacid S methyl ester diacetate, prepared by treating octahydroacid S methyl ester (1 equivalent) with acetic anhydride (100 equivalents) and pyridine (200 equivalents) at room temperature for 16 hours, and having the following characteristics:
   a. Infrared Spectrum $\nu_{max}$ 1740, 1440, 1370, 1250, 1230, 1050 and 920 cm$^{-1}$.
   b. Mass Spectrum m/e (relative intensity) 582 (5), 580 (20), 578 (7), 520 (15), 460 (15), 367 (12), 337 (17), 214 (45), 197 (35), 167 (100), 154 (100) 143 (50), 127 (50) and 109 (45).
   c. Molecular Formula $C_{33}H_{56}O_8$; molecular weight 580.

6. An antimicrobial substance, octahydrotriol S triacetate, prepared by treating octahydrotriol S (1 equivalent) with acetic anhydride (100 equivalents) and pyridine (200 equivalents) at room temperature for 16 hours, and having the following characteristics:
   a. Infrared Spectrum $\nu_{max}$ 1750, 1450, 1370, 1240, 1300 and 1240 cm$^{-1}$.
   b. Mass Spectrum m/e (relative intensity) 596 (1), 594 (4), 592 (2), 167 (83), 154 (100), 127 (22) and 109 (16).
   c. Molecular Formula $C_{34}H_{58}O_8$; molecular weight 594.

7. An antimicrobial substance, decahydroacid S, prepared by stirring a 1 percent ethanolic solution of acid S with hydrogen in the presence of 10 percent palladium-on-carbon for 4 hours and having the following characteristics:
   a. Infrared Spectrum $\nu_{max}$ 3350, 1720, 1470, 1380, 1080 and 960 cm$^{-1}$.
   b. Molecular Formula $C_{28}H_{52}O_6$; molecular weight 484.

8. An antimicrobial substance, decahydroacid S methyl ester, prepared by treating a 1 percent ethanolic solution of decahydroacid S (1 equivalent) with ethereal diazomethane (12 equivalents) and having the following characteristics:
   a. Infrared Spectrum $\nu_{max}$ 3350, 1740, 1470, 1450, 1380, 1210 and 1080 cm$^{-1}$.
   b. Mass Spectrum m/e (relative intensity) 498 (4), 373 (2), 339 (7), 167 (9), 154 (63), 142 (14), 127 (100) and 109 (34).
   c. Molecular Formula $C_{29}H_{54}O_6$; molecular weight 498.

9. An antimicrobial substance, decahydrotriol S, prepared by stirring a 1 percent ethanolic solution of triol S with hydrogen in the presence of 10% palladium-on-carbon for 4 hours and having the following characteristics:
   a. Infrared Spectrum $\nu_{max}$ 3350, 1470, 1390, and 1080 cm$^{-1}$.
   b. Mass Spectrum m/e (relative intensity) 470 (4), 339 (7), 315 (4), 297 (6), 154 (15), 127 (100) and 109 (60).
   c. Molecular Formula $C_{28}H_{54}O_5$; molecular weight 470.

10. An antimicrobial substance, decahydroacid S diacetate, prepared by treating decahydroacid S (1 equivalent) with acetic anhydride (100 equivalents) and pyridine (200 equivalents) at room temperature for 16 hours and having the following characteristics:
    a. Infrared Spectrum $\nu_{max}$ 1740, 1470, 1380, 1250 and 1060 cm$^{-1}$.
    b. Mass Spectrum m/e (relative intensity) 568 (12.5) 167 (20), 154 (70), 127 (100) and 109 (60).
    c. Molecular Formula $C_{32}H_{56}O_8$; molecular weight 568.

11. An antimicrobial substance, decahydroacid S methyl ester diacetate, prepared by treating decahydroacid S methyl ester (1 equivalent) with acetic anhydride (100 equivalents) in pyridine (200 equivalents at room temperature for 16 hours and having the following characteristics:
    a. Infrared Spectrum $\nu_{max}$ 1740, 1470, 1380, 1240, 1090, 1050 and 920 cm$^{-1}$.
    b. Mass Spectrum m/e (relative intensity) 582 (8), 522 (4), 506 (1), 367 (5), 223 (5), 201 (4), 167 (8), 154 (36), 127 (100) and 109 (36); molecular ion observed: 582.4130; calculated for $C_{33}H_{58}O_8$: 582.4131.

12. An antimicrobial substance, decahydrotriol S triacetate, prepared by treating decahydrotriol S (1 equivalent) with acetic anhydride (100 equivalents) and pyridine (200 equivalents) at room temperature for 16 hours and having the following characteristics:
    a. Infrared Spectrum $\nu_{max}$ 1740, 1460, 1380, 1240, 1090, 1040 and 910 cm$^{-1}$.
    b. Mass Spectrum m/e (relative intensity) 596 (6), 536 (5), 520 (2), 476 (3), 462 (4), 441 (4), 381 (3.5), 237 (4), 215 (4), 199 (18), 167 (7), 154 (25), 127 (100) and 109 (42); molecular ion observed: 596.4355; calculated for $C_{34}H_{60}O_8$: 596.4288.

13. An antimicrobial substance, acid S diacetate, prepared by treating acid S (1 equivalent) with acetic anhydride (100 equivalents) and pyridine (200 equivalents) at room temperature for 16 hours and having the following characteristics:
    a. Mass Spectrum m/e (relative intensity) 558 (10), 529 (32), 463 (14), 345 (7), 245 (32), 193 (100) and 165 (57).
    b. Infrared Spectrum $\nu_{max}$ 1745, 1720, 1460, 1380, 1250, 1060, 970 and 760 cm$^{-1}$.
    c. Molecular Formula $C_{32}H_{46}O_8$; molecular weight 558.

14. An antimicrobial substance, acid S methyl ester diacetate, prepared by treating acid S methyl ester (1 equivalent) with acetic anhydride (100 equivalents) and pyridine (200 equivalents) at room temperature for 16 hours and having the following characteristics:
    a. Infrared Spectrum $\nu_{max}$ 1760, 1440, 1370, 1240, 1050 and 960 cm$^{-1}$.
    b. Mass Spectrum m/e (relative intensity) 572 (23), 543 (53), 477 (29), 259 (35) and 193 (100).
    c. Molecular Formula $C_{33}H_{48}O_8$; molecular weight 572.

* * * * *